US009956107B2

(12) United States Patent
Blanck

(10) Patent No.: US 9,956,107 B2
(45) Date of Patent: May 1, 2018

(54) DYNAMIC EXOSKELETAL ORTHOSIS

(71) Applicant: The United States of America As Represented By the Secretary of the Army, Washington, DC (US)

(72) Inventor: Ryan Vaughn Blanck, Schertz, TX (US)

(73) Assignee: The United States of America as represented by The Secretary of the Army, Washington, DC (US)

( * ) Notice: Subject to any disclaimer, the term of this patent is extended or adjusted under 35 U.S.C. 154(b) by 96 days.

(21) Appl. No.: 13/773,776

(22) Filed: Feb. 22, 2013

(65) Prior Publication Data

US 2013/0165833 A1 Jun. 27, 2013

Related U.S. Application Data

(63) Continuation-in-part of application No. 13/450,539, filed on Apr. 19, 2012, now Pat. No. 9,186,270.

(60) Provisional application No. 61/518,801, filed on Apr. 20, 2011.

(51) Int. Cl.
*A61F 5/00* (2006.01)
*A61F 5/01* (2006.01)

(52) U.S. Cl.
CPC .................. *A61F 5/0127* (2013.01)

(58) Field of Classification Search
CPC ........ A61F 5/01; A61F 5/0102; A61F 5/0104; A61F 5/0111; A61F 5/0113; A61F 5/0127; A61F 5/00; A61F 5/0106; A61F 5/0109; A61F 5/0123; A61F 5/0125; A61F 2005/0132; A61F 2005/0179; A61F 5/05841; A61F 5/0585

USPC ................... 128/869, 882; 602/5, 23, 26, 27
See application file for complete search history.

(56) References Cited

U.S. PATENT DOCUMENTS

| | | | | |
|---|---|---|---|---|
| 1,769,681 | A | * | 7/1930 | Ettinger ........................ 602/23 |
| 2,796,866 | A | * | 6/1957 | Cohen .......................... 128/869 |
| RE30,501 | E | | 2/1981 | Almeida |
| 4,991,571 | A | * | 2/1991 | Kausek .......................... 602/16 |
| 5,088,479 | A | * | 2/1992 | Detoro ........................... 602/27 |
| 5,344,390 | A | * | 9/1994 | Motloch ........................ 602/23 |
| 5,529,576 | A | | 6/1996 | Lundt et al. |
| 5,981,112 | A | | 11/1999 | Roberts |
| 6,007,506 | A | | 12/1999 | Heil |
| 6,010,474 | A | | 1/2000 | Wycoki |
| RE37,209 | E | * | 6/2001 | Hensley et al. ............... 602/26 |
| 6,537,238 | B1 | * | 3/2003 | Chignon ........................ 602/23 |
| 6,793,638 | B1 | * | 9/2004 | DeToro et al. ................ 602/23 |
| 6,827,696 | B1 | * | 12/2004 | Maguire ........................ 602/27 |
| 6,945,946 | B2 | * | 9/2005 | Rooney .......................... 602/27 |
| 6,946,946 | B2 | | 9/2005 | Buswell |
| 7,112,180 | B2 | * | 9/2006 | Guenther ...................... 602/23 |

(Continued)

OTHER PUBLICATIONS

Galvan, S., et al., "Orthopedic Device Helping Wounded Warriors Return to Run," Aug. 12, 2011.

(Continued)

*Primary Examiner* — Ophelia A Hawthorne
*Assistant Examiner* — Caitlin Carreiro
(74) *Attorney, Agent, or Firm* — Elizabeth Arwine, Esq.

(57) ABSTRACT

An exoskeletal orthosis includes a proximal cuff includes a hinge along an upper edge of the cuff; an ankle section/footplate; and at least one posterior strut connecting the proximal cuff to the ankle section and foot plate.

5 Claims, 12 Drawing Sheets

(56) References Cited

U.S. PATENT DOCUMENTS

| | | | |
|---|---|---|---|
| 7,270,644 B2* | 9/2007 | Ingimundarson | 602/27 |
| 7,462,160 B2* | 12/2008 | Nobbe et al. | 602/27 |
| 7,513,880 B2* | 4/2009 | Ingimundarson et al. | 602/23 |
| 7,727,173 B2* | 6/2010 | Rooney | 602/23 |
| 7,819,832 B2 | 10/2010 | Balzer | |
| 8,425,440 B2* | 4/2013 | DeToro et al. | 602/16 |
| 8,465,445 B2* | 6/2013 | George | 602/23 |
| 8,480,604 B2* | 7/2013 | Messer | 602/6 |
| 2005/0137510 A1 | 6/2005 | Dauny | |
| 2006/0079822 A1* | 4/2006 | Hjorth | 602/28 |
| 2006/0270958 A1* | 11/2006 | George | 602/28 |
| 2006/0276736 A1* | 12/2006 | Devreese | 602/27 |
| 2007/0027421 A1 | 2/2007 | Nobbe et al. | |
| 2009/0198164 A1* | 8/2009 | Krause | A61F 5/0123 602/26 |
| 2009/0292229 A1* | 11/2009 | Nace | 602/16 |
| 2010/0030123 A1* | 2/2010 | DeToro et al. | 602/28 |
| 2010/0056970 A1* | 3/2010 | Nace | 602/26 |
| 2010/0101118 A1* | 4/2010 | Guenther | 36/140 |
| 2010/0204631 A1* | 8/2010 | Rooney | 602/23 |
| 2012/0271214 A1 | 10/2012 | Blanck | |
| 2013/0165833 A1 | 6/2013 | Blanck | |

OTHER PUBLICATIONS

Marini, R., "GIs Bracing for New Action," http://www.express-news.net, Sep. 4, 2011.

Masulli, J., http://www.njherald.com/story/news/.

Owens, J., et al., Return to Running and Sports Participation After Limb Salvage, The Journal of Trauma Injury, Infection, and Critical Care, Jul. 2011, Jul. 2011, vol. 71, No. 1.

Patzkowski, J., et al., "Can an Ankle-Foot Orthosis Change Hearts and Minds?", Journal of Surgical Orthopaedic Advances, 2011, pp. 8-18, vol. 20, No. 1.

Rigby, W., "Up and Running: Device Readies Wounded Warriors for Action," Kens 5 San Antonio, Aug. 12, 2011.

Robbins, S., "Device Might Offer Some Troops an Alternative to Amputation," Stars and Stripes, Sep. 21, 2011.

Sanchez, E., New Brace Salvages Limbs, Mobility, Morale, Defense.gov, Dec. 8, 2011.

Tan, M., "Damaged Legs Made Fit," Army Times, Aug. 29, 2011.

Patzkowski, J., et al., "Comparative Effect of Orthosis Design on Functional Performance," The Journal of Bone and Joint Surgery, 2012, pp. 507-515, vol. 94.

Notification Concerning Transmittal of International Preliminary Report on Patentability dated Oct. 30, 2014.

Judd Lundt et al., "The USMC Strut Technology Applied to AFOs", American Academy of Orthotists and Prosthetists, Journal of Proceedings, 2000.

Judd Lundt et al., "The USMC LITTIG Dynamic Response Hip, Redesigned", American Academy of Orthotists and Prosthetists, Journal of Proceedings, 2000.

Future Design Fabrications: Custom Prosthetics and Orthotic Devices. http://www.futuredesignfabrications.com/orthotics.html, printed on Oct. 1, 2014.

\* cited by examiner

FIG. 5
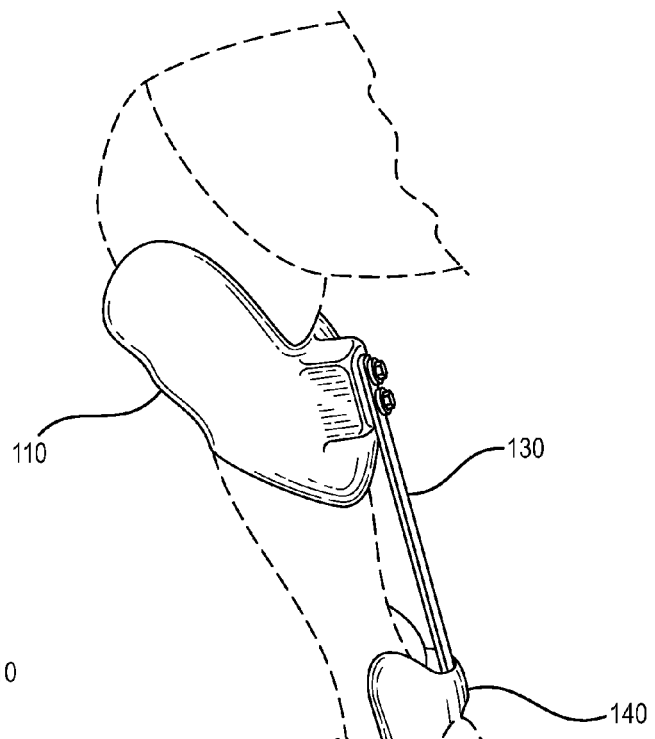
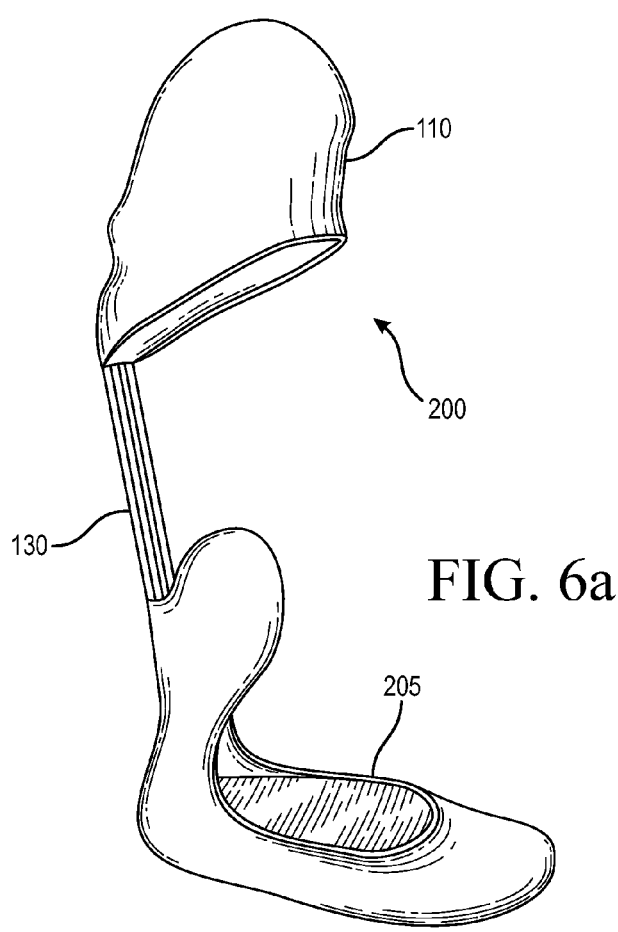
FIG. 6a

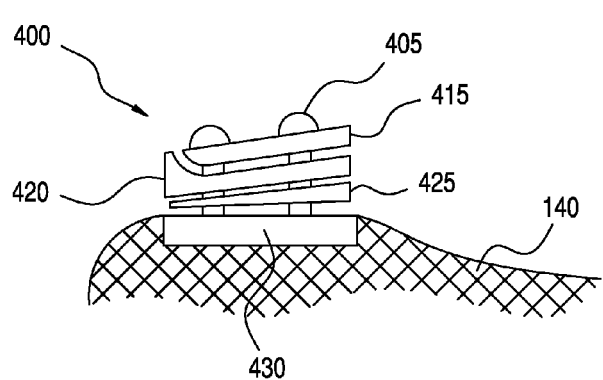
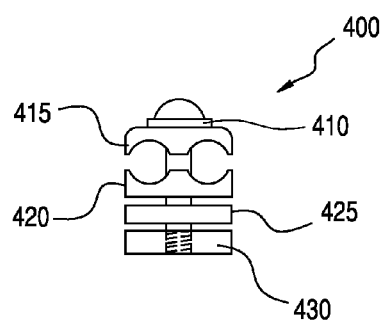
FIG. 16a  FIG. 16b
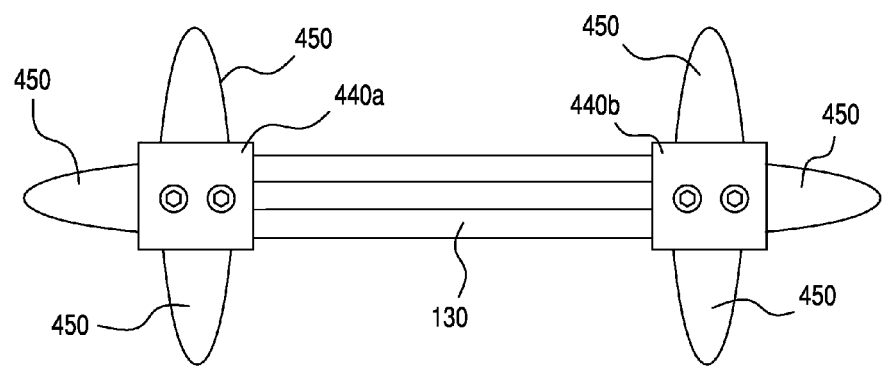
FIG. 17

DYNAMIC EXOSKELETAL ORTHOSIS

RELATED APPLICATIONS

This application is a Continuation-In-Part application of U.S. Ser. No. 13/450,539, filed on Apr. 19, 2012, which claims priority to U.S. Provisional Patent Application Ser. No. 61/518,801 filed in the U.S. Patent and Trademark Office on Apr. 20, 2011, the entireties of which are incorporated herein by reference.

FIELD OF INVENTION

The present invention is directed to an ankle foot orthosis or brace, in particular to a dynamic exoskeletal orthosis.

BACKGROUND

Orthotics are devices that are made to correct or maintain alignment of different parts of the body, hence the name "braces."

An ankle foot orthosis (AFO) supports the joints of the foot, as well as the ankle. These devices can be used to protect, correct or limit motion at the joints by supporting a person's limb that has suffered from loss of strength or alignment due to disease or trauma. AFOs can be a solid design at the ankle with no motion allowed, or with joints to allow certain degrees of motion.

Historically, bracing options for those with pain/weakness/decreased range of motion about the ankle have been severely limited. The most common types of bracing either provided adequate strength compensation in the instance of an isolated peroneal neuropathy or were designed with very stiff orthotic materials that essentially immobilized the ankle and did not allow a more normal gait or higher level activities.

SUMMARY OF INVENTION

According to an aspect of the present invention, an exoskeletal orthosis comprises a proximal cuff comprising a hinge along an upper edge of the cuff; an ankle section/footplate; and at least one posterior strut connecting the proximal cuff to the ankle section/footplate.

According to another aspect of the present invention an orthosis comprises a proximal cuff comprising at least one hinge along an upper edge of the cuff; an ankle section/footplate; and at least one posterior strut attached at a proximal end to the proximal cuff and attached at a distal end to the ankle section/footplate. The ankle section/footplate comprises a supramalleolar ankle section having a lateral wing and a footplate section extending to the tips of a user's toes and having an arch.

According to another aspect of the invention, a method of treating an injury is provided comprising fitting an individual having an injury with an orthosis according to the present invention and placing the individual's foot with the attached orthosis inside a shoe or boot.

According to yet another aspect of the present invention, an orthosis comprises a proximal cuff; an ankle section/footplate; and a single posterior strut connecting a rear of the proximal cuff to a rear of the ankle section/footplate.

According to still another aspect of the present invention, a knee ankle foot exoskeletal orthosis comprises a proximal cuff; an ankle section/footplate; dual posterior struts connecting a rear of the proximal cuff to a rear of the ankle section/footplate, and an upper knee orthosis section connected to the proximal cuff and comprising at least one stretchable band affixed on each side.

According to a further aspect of the present invention, an alignable exoskeletal orthosis comprises a proximal cuff; an ankle section/footplate; and at least one posterior strut connecting a rear of the proximal cuff to a rear of the ankle section/footplate. The at least one posterior strut is fixed onto at least one of the ankle/footplate or the posterior cuff via a bolt mechanism comprising at least one angled wedge.

According to a further aspect of the present invention, an exoskeletal orthosis comprises a proximal cuff; an ankle section/footplate; and at least one posterior strut connected to a rear of the proximal cuff via an upper mounting plate and connected to a rear of the ankle section/footplate via a low mounting plate. The upper and lower mounting plates each have moldable flaps or wings extending from the sides thereof.

An advantage of the present invention is that the dynamic exoskeletal orthosis allows greater ability to walk and run despite severe lower extremity physical impairments.

Another advantage of the present invention is that the dynamic exoskeletal orthosis allows for early walking post-injury to high level activities with the same orthosis.

Yet another advantage of the present invention is that the dynamic exoskeletal orthosis may be lightweight, durable (tolerates impact of running with a ruck sack, for example, up to about 120 lbs.), and may be used in regular shoes and military boots.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

BRIEF DESCRIPTION OF THE DRAWINGS

FIG. 5 is a view of a dynamic exoskeletal orthosis attached to a person's leg and foot.

FIG. 6a is a side view of a partial dynamic exoskeletal orthosis according to an embodiment of the present invention.

FIG. 6b is a top view of the partial dynamic exoskeletal orthosis of FIG. 6a.

FIG. 16a is a side view of a bolt mechanism for an alignable configuration of an exoskeletal orthosis according to an embodiment of the present invention.

FIG. 16b is a top view of the bolt mechanism of FIG. 16a.

FIG. 17 shows dual posterior struts and mounting plates for a non-alignable configuration of an exoskeletal orthosis according to an embodiment of the present invention.

Given the following enabling description of the drawings, the methods and apparatus should become evident to a person of ordinary skill in the art.

DETAILED DESCRIPTION OF INVENTION

The orthosis of the present invention is designed to allow walking and running for individuals or patients with severe injury to the lower limb that causes reduced ankle range of motion, weakness, and pain. The orthosis allows for a range of activities including, but not limited to, at least one of early ambulation during an early post-injury phase, agility and impact activities, running, sprinting, or deploying with a military unit.

The orthosis of the present invention is designed to compensate for weakness, pain, and/or decreased range of motion (either alone or in combination) at the ankle that result from a variety of potential diagnoses including, but not limited to, at least one of ankle fusion, talus or calcaneus fractures, tibial nerve injuries, peroneal nerve injuries, partial foot amputation (which results in ankle plantarflexion weakness), soft tissue loss in the leg (resulting in inherent weakness), or pain in the ankle during weight bearing activities.

Current research suggests that the orthosis of the present invention not only compensates for weakness, but also generates forces about the ankle that more closely approaches the normal gait than other currently available orthoses. The article Patzowski et al., *Comparative Effect of Orthosis Design on Functional Performance*, J. Bone Joint Surg. Ab., 2012; 94:507-15, is incorporated by reference herein in its entirety. The article Patzowski et al., *Can an Ankle-Foot Orthosis Change Hearts and Minds?*", J. Surgical Orthopaedic Advances, 20(1):8-18, 2011, is also incorporated by reference herein in its entirety.

In specific embodiments, the orthosis of the present invention may be applied to the leg below the knee. The orthosis (also referred to as the Intrepid Dynamic Exoskeletal Orthosis or IDEO) may comprise the following components (description from an upper/proximal aspect to a lower/distal aspect).

A. Proximal Cuff

Figure 1:
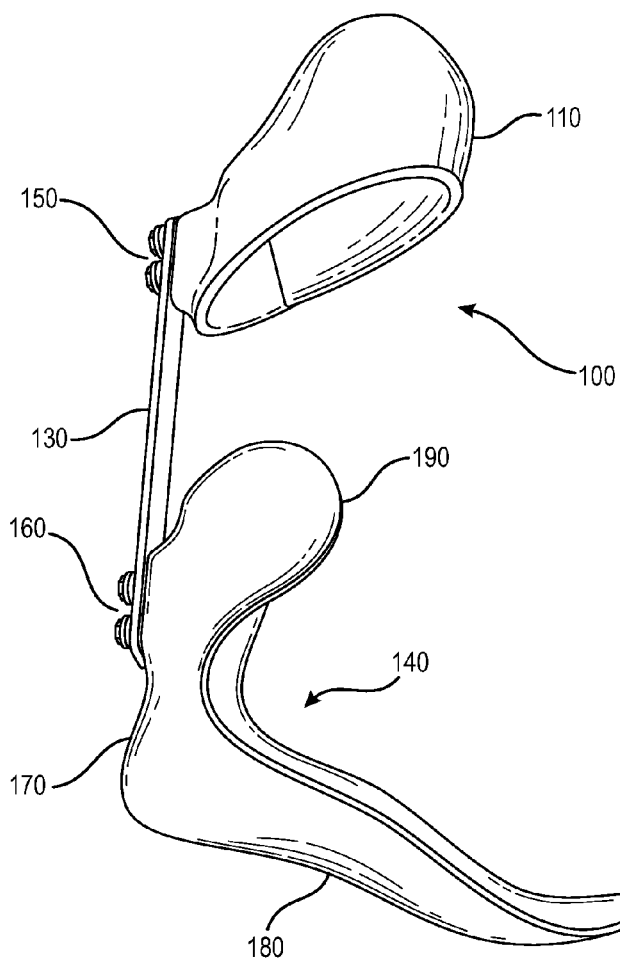
FIG. 1 is a side view of a dynamic exoskeletal orthosis according to an embodiment of the present invention.

With reference now to FIG. 1, the exoskeletal orthosis 100 according to the present invention comprises a proximal cuff 110. The proximal cuff may comprise at least one of a carbon material, reinforced carbon fiber composition, or resin material. The cuff may have a bivalve or a monolithic configuration.

A monolithic, one-piece, solid configuration comprises a solid cuff and is designed for a patient who has a stable size of the upper leg (calf and shin) and does not have limited ankle plantarflexion.

Figure 2:
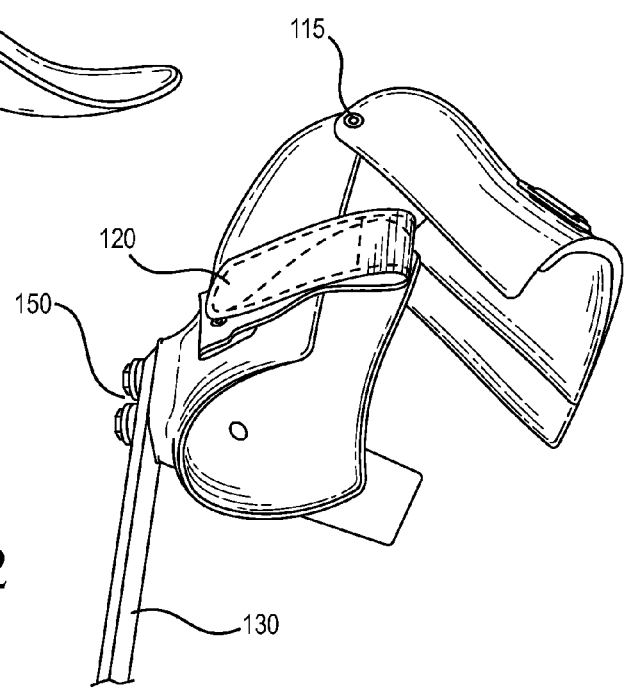
FIG. 2 is a view of a proximal cuff of a dynamic exoskeletal orthosis according to an embodiment of the present invention.
Figure 3:
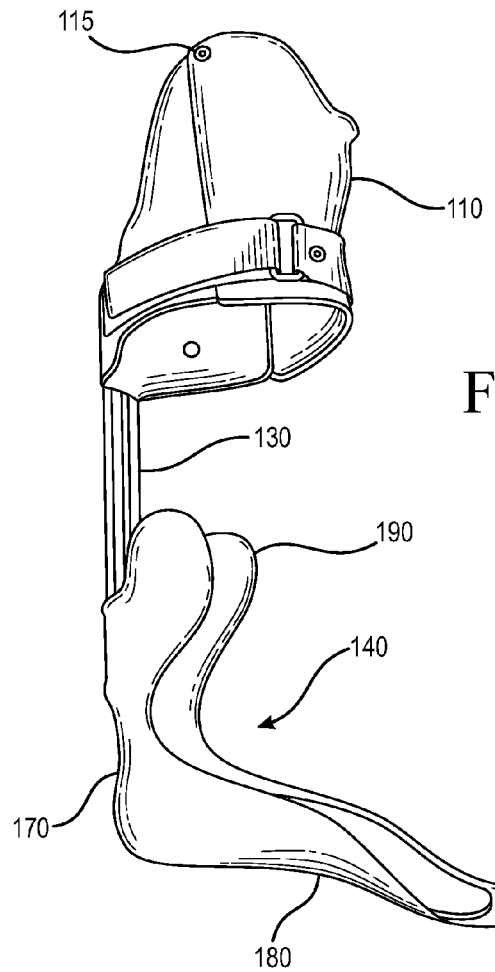
FIG. 3 is a view of a dynamic exoskeletal having a dual strut configuration according to another embodiment of the present invention.

In specific embodiments, the proximal cuff may comprise a two piece or bivalve cuff having a hinge 115 (as shown in FIGS. 2-3) along an upper edge or aspect, thereby allowing the proximal cuff 110 to have a wider opening distally when donning the brace. This configuration may be utilized for patients who are not able to plantarflex the ankle enough to fit through a monolithic (solid) configuration and also allows for volume fluctuation of the upper leg. The hinge 115 allows the proximal cuff 110 to open upward due to a proximal fixed axis point (see FIG. 2).

In one or more embodiments, the proximal cuff 100 may have a strap 120 to help hold it in place while in use.

B. Posterior Strut

The exoskeletal orthosis 100 comprises at least one posterior strut 130 for connecting the proximal cuff 110 to an ankle/footplate section 140. The at least one posterior strut 130 may comprise a single bar (e.g., FIG. 1) or dual bars (e.g., FIG. 3), which may be bonded together. The at least one posterior strut may be of any shape for example, a flat bar, a cylindrical or tubular shape, or having a circular or semi-circular cross section. In one or more embodiments, the at least on posterior strut 130 may have a length of about 5 inches to about 13 inches (12.7 cm to 33 cm).

In specific embodiments, the at least one posterior strut 130 may comprise an alignable dynamic carbon strut, for example, a TRULIFE Littig strut or a MEDI CLEVER BONE™ strut. The Littig strut was originally designed for use in the upper portion of hip disarticulation prostheses. The MEDI CLEVER BONE™ strut (bone system) may be designed for use as a dynamic pylon for transtibial prostheses.

The at least on posterior strut 130 may comprise at least one of a carbon material, reinforced carbon fiber composition, or resin material. In a specific embodiment, the at least one posterior strut may have an Aerolon core.

In one or more embodiments, the at least on posterior strut may comprise an SLS material. Selective laser sintering (SLS) is an additive manufacturing technique that uses a high power laser (for example, a carbon dioxide laser) to fuse small particles of plastic, metal (direct metal laser sintering), ceramic, or glass powders into a mass that has a desired 3-dimensional shape.

C. Mounting Plates

Figure 4:
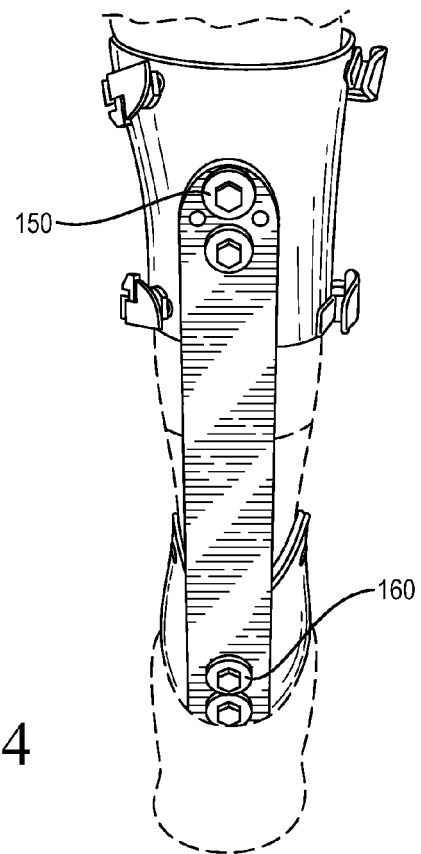
FIG. 4 is a rear view of a dynamic exoskeletal orthosis showing a posterior strut according to an embodiment of the present invention.

The exoskeletal orthosis 100 may comprise at least one mounting plate, for example, two mounting plates: a first mounting plate 150 for attaching one end of the at least one posterior strut 130 to the proximal cuff and a second mounting plate 160 for attaching an opposite end of the at least one posterior strut 130 to the ankle section/footplate 140 (as shown in FIGS. 1 and 4). In one or more embodiments, the at least one mounting plate may comprise an ÖSSUR® posterior mounting plate (designed for transtibial prostheses).

The mounting plates 150, 160 may include a fastener including, but not limited to, at least one of a screw, bolt, nail, nut, adhesive, combination thereof, or any other effective fastener.

The attachment of the at least one posterior strut 130 to an ankle section/footplate 140 may be slightly more proximal than traditional orthoses. This helps offset motion within the ankle, which is often painful or severely limited in these patients, to the at least one posterior strut without compromising comfort.

D. Ankle Section/Footplate

The exoskeletal orthosis 100 comprises an ankle section/footplate 140. The ankle section/footplate comprises a supramalleolar ankle section 170 and footplate section 180 (e.g., FIG. 1). The ankle section/footplate 140 may be a single piece comprising a reinforced carbon fiber composition. In one or more embodiments, the ankle section 170 comprises a lateral wing 190 for mediolateral stability and for fitting better in shoes or boots (FIG. 5). In one or more embodiments, the ankle section may also have a medial wing.

In one or more embodiments, the footplate section 180 has a "rollover" shape (e.g., FIG. 1 and FIG. 3). The shape of the footplate section 180 positions an individual's toes in slight extension and extends to his or her toetips. A forefoot (end of the footplate) is set in slight plantarflexion compared to a midfoot. In one or more embodiments, the ankle section/footplate 140 may be stiff due to the layering of materials and carbon fiber. The footplate section 180 may have an arch (instead of being completely flat) and have extension at the metatarsophalangeal joints, which enables the metatarsal heads to remain in contact with the ground for a longer duration during ambulation.

The plantar surface of the footplate allows optimal function of the at least one posterior strut and long-term durability of the orthosis. As noted, the footplate section may have a gradual roller shape that begins just distal to a heel, which may have a cushion. In one or more embodiment, a portion of the heel, for example a posterior heel base, may comprise a SACH heel (solid ankle cushion heel).

During heel strike, the heel decreases impact on the limb and allows the patient to easily bring the forefoot to a floor. A cushioned heel may allow a gradually increasing load to the posterior strut as the tibia moves forward, while the plantarflexed foot position increases the degree of deflection and amount of energy storage from midstance through terminal stance. Energy storage and return is evident during agility drills, running, and sprinting activities, which are primarily performed while up on the forefoot. A distal third of the plantar surface may have a dorsiflexion radius design that maintains solid metatarsal contact to the ground for increased proprioception and control.

In a specific embodiment, the alignment of the orthosis can be adjusted on average up to about 7° of dorsiflexion, plantarflexion, and external or internal rotation and about 5° of inversion or eversion.

E. Versions of the Exoskeletal Orthosis

In a specific embodiment, the orthosis may comprise cushioned foam attached to a proximal sole on a bottom portion the ankle section/footplate. The cushioned foam may be an entirely different and separate component from the orthosis, as the foam may require fabrication by a specially trained orthotist (preferably prosthetist-orthotist) and orthotic technician. Thickness and density of the foam are specific to a patient's relative ankle position, injury, weight, height, and activity level.

In embodiments, the orthosis may be made from modular components or fixed components. A modular version may be used during initial fittings and may be modified as patients progress during their rehabilitation, for example, progressing from a softer strut to a stiffer strut as they become stronger. The modular version may also include an external fixator (e.g., fastener and mounting plates).

In a specific embodiment, a modular version may comprise a flat bar (e.g., TRULIFE Littig) posterior strut. The posteriorly mounted 'run plate' may be utilized in a posterior-mounted running prosthesis. The alignment of the ankle section/footplate may also be modifiable. The angle of the footplate may be adjusted within 6 different planes, similar to adjustments for a prosthesis, in relation to a patient's foot and leg. In specific embodiments, the modular version may have a posterior strut that is attached to the proximal cuff proximally via an ÖSSUR® posterior mounted run plate with two bolts, plus a second ÖSSUR® posterior mounted run plate with two bolts at the distal end of the posterior strut (FIGS. 1-2).

In a specific embodiment, a fixed version may comprise a dual bar strut (e.g., MEDI CLEVER BONE™) for an overall lighter weight of the brace, use for higher loading and impact activities (greater durability), and the capacity for twisting motions of the lower leg. The fixed version allows for use inside boots and tighter clothing about the legs. The dual bar strut may be permanently attached (bonded) to the proximal cuff proximally and the foot/ankle component distally (as shown in FIG. 3). The fixed version may allow an inherent torsional component and accommodates twisting motions more than the modular version. The fixed version has subjectively shown an increased energy return and improved high intensity performance associated with its springlike effect, per verbal accounts from patients. However, it may be possible to use a dual posterior strut configuration in a modular version.

F. Partial Foot Embodiment

Figure 6B:
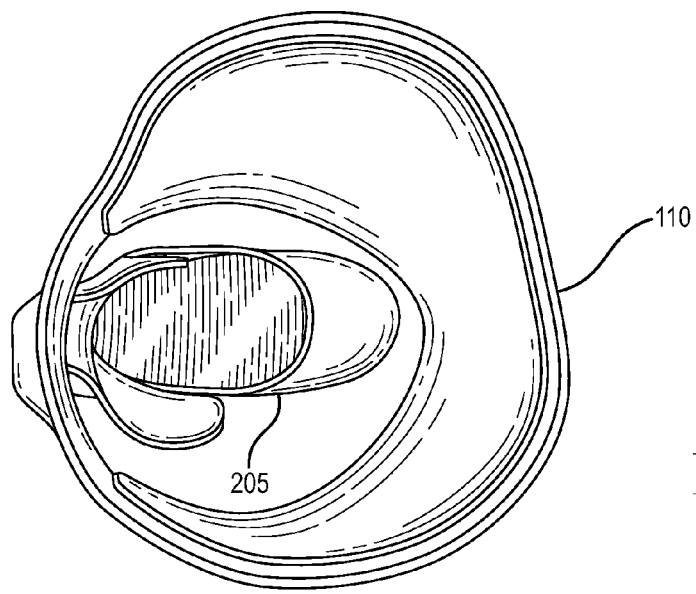

With reference now to FIGS. 6*a-b*, a partial foot orthosis 200 may be applied to individuals with amputation of part of the foot. The partial foot exoskeletal orthosis 200 may have a similar construction to the orthosis 100 discussed above. The partial foot orthosis 200 has a circumferential configuration of the footplate 205 (extending around the area of the foot that was amputated).

Figure 7:
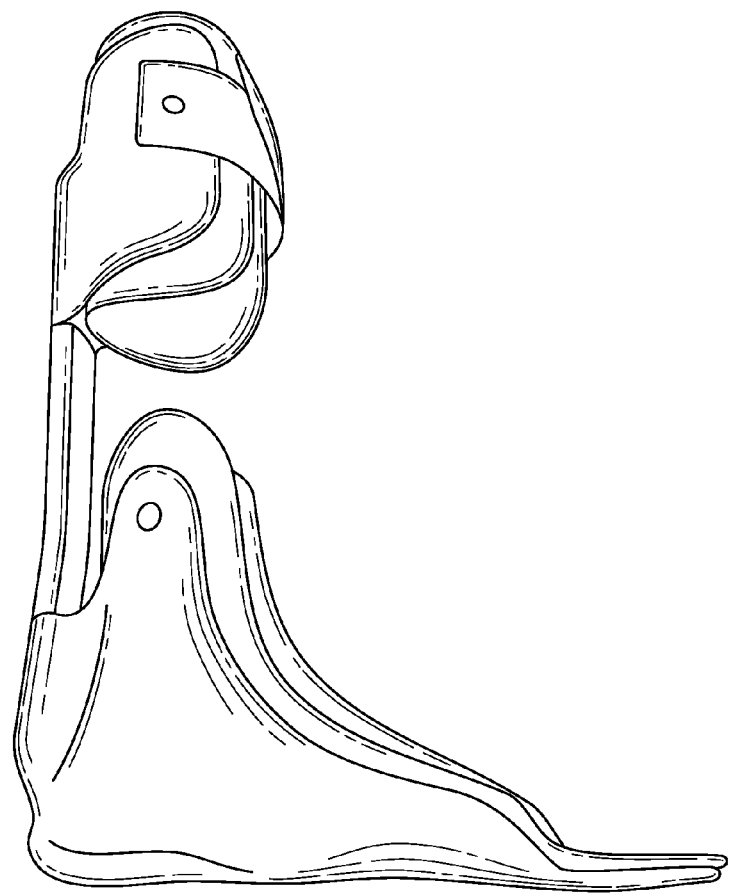
FIG. 7 is a side view of a dynamic exoskeletal orthosis according to another embodiment of the present invention.

With reference now to FIG. 7, another embodiment of the orthosis 100 is shown in which at least one of the proximal cuff 110 or ankle section/footplate 140 comprise a laminate material.

G. Knee Ankle Foot Orthosis

Figure 8:
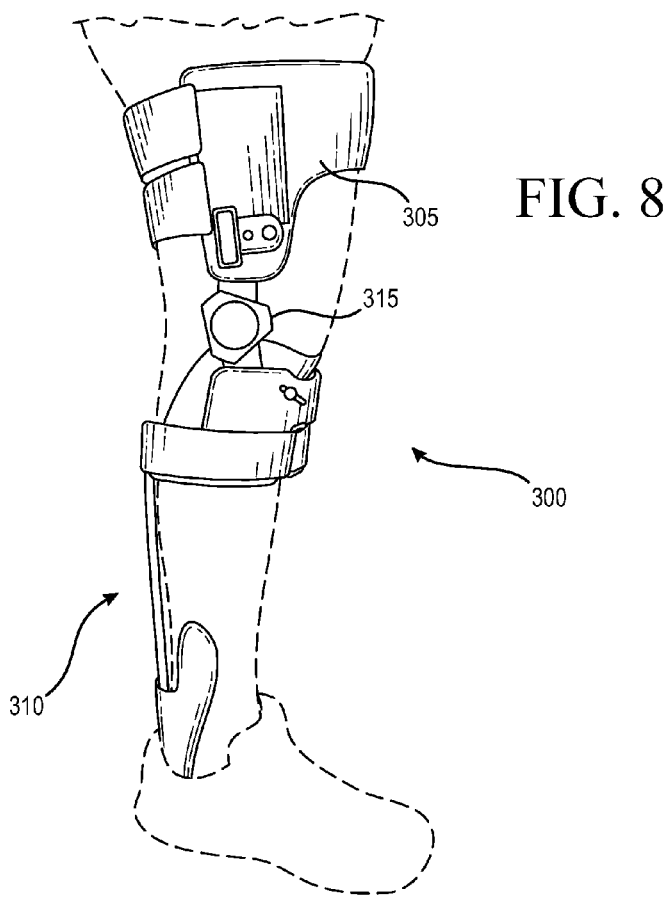
FIG. 8 is a side view of a dynamic knee ankle foot exoskeletal orthosis according to an embodiment of the present invention.
Figure 9:
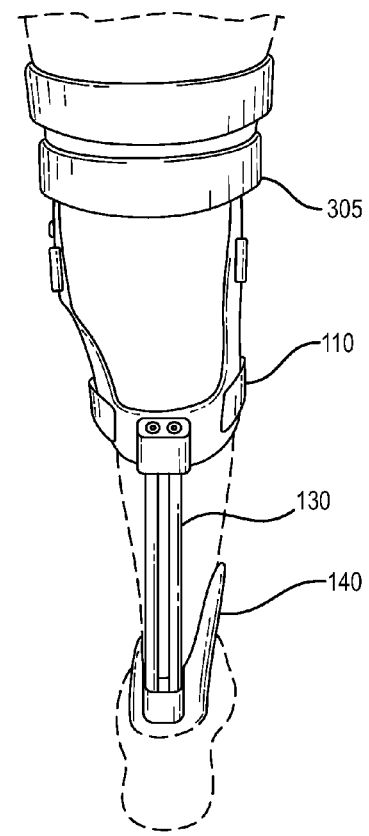
FIG. 9 is a rear view of a dynamic knee ankle foot exoskeletal orthosis according to an embodiment of the present invention.

With reference now to FIGS. 8-9, an embodiment of the present invention directed to a knee ankle foot orthosis 300 is shown. In one or more embodiments, the knee ankle foot orthosis 300 may comprise a modular removable fabricated version that allows a patient to attach or detach a knee orthosis section 305 to an ankle foot orthosis (AFO) section 310 depending on desired activity and limb stability needs.

In one or more embodiments, the knee ankle orthosis 300 may comprise a fixed version comprising a connector or hinge 315 (e.g., Tm5 or original TOWNSEND stainless steel knee hinge) in which the upper knee orthosis section 305 is connected or fused to the lower ankle foot orthosis section 310.

The knee ankle foot orthosis may be either modular or fixed, and may be used for varying weaknesses, nerve injuries, ligamentous injuries, proximal knee or femoral fx's histories to allow a patient to walk, run, or perform some level of high impact activity with greater function and increased safety.

Knee ankle foot orthosis versions, both modular and fixed, may also be used for dynamic exoskeletal orthosis cases deploying and participating in fast rope helicopter jumps, static line parachuting, or standard parachuting maneuvers to prevent potential knee injuries while using the dynamic exoskeletal orthosis for prior injury of the ankle, nerve, and the like.

H. Single Strut Embodiment

Figure 10:
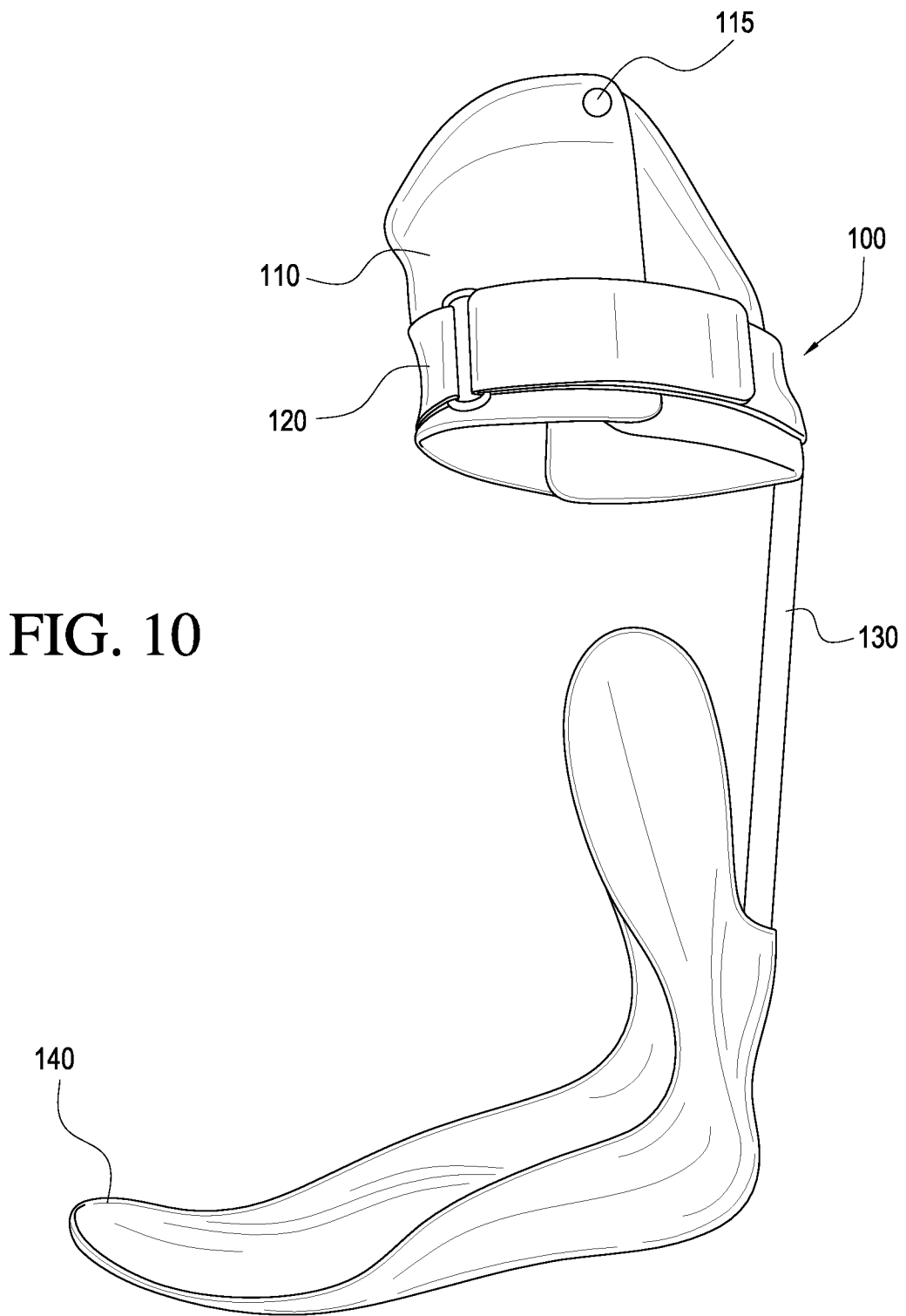
FIG. 10 is a side view of a dynamic exoskeletal orthosis according to another embodiment of the present invention.
Figure 11:
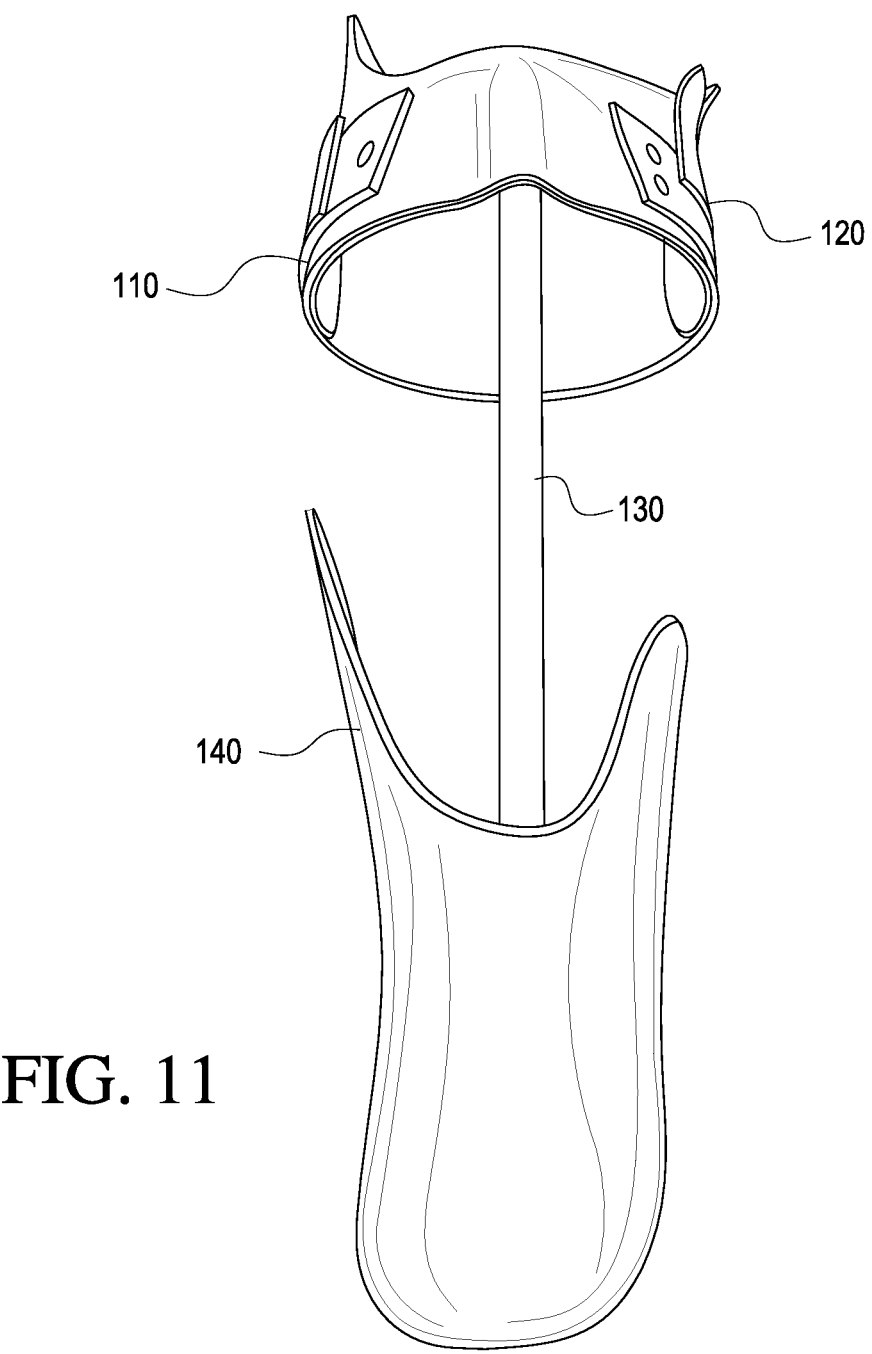
FIG. 11 is a rear view of a dynamic exoskeletal orthosis of FIG. 10.
Figure 12:
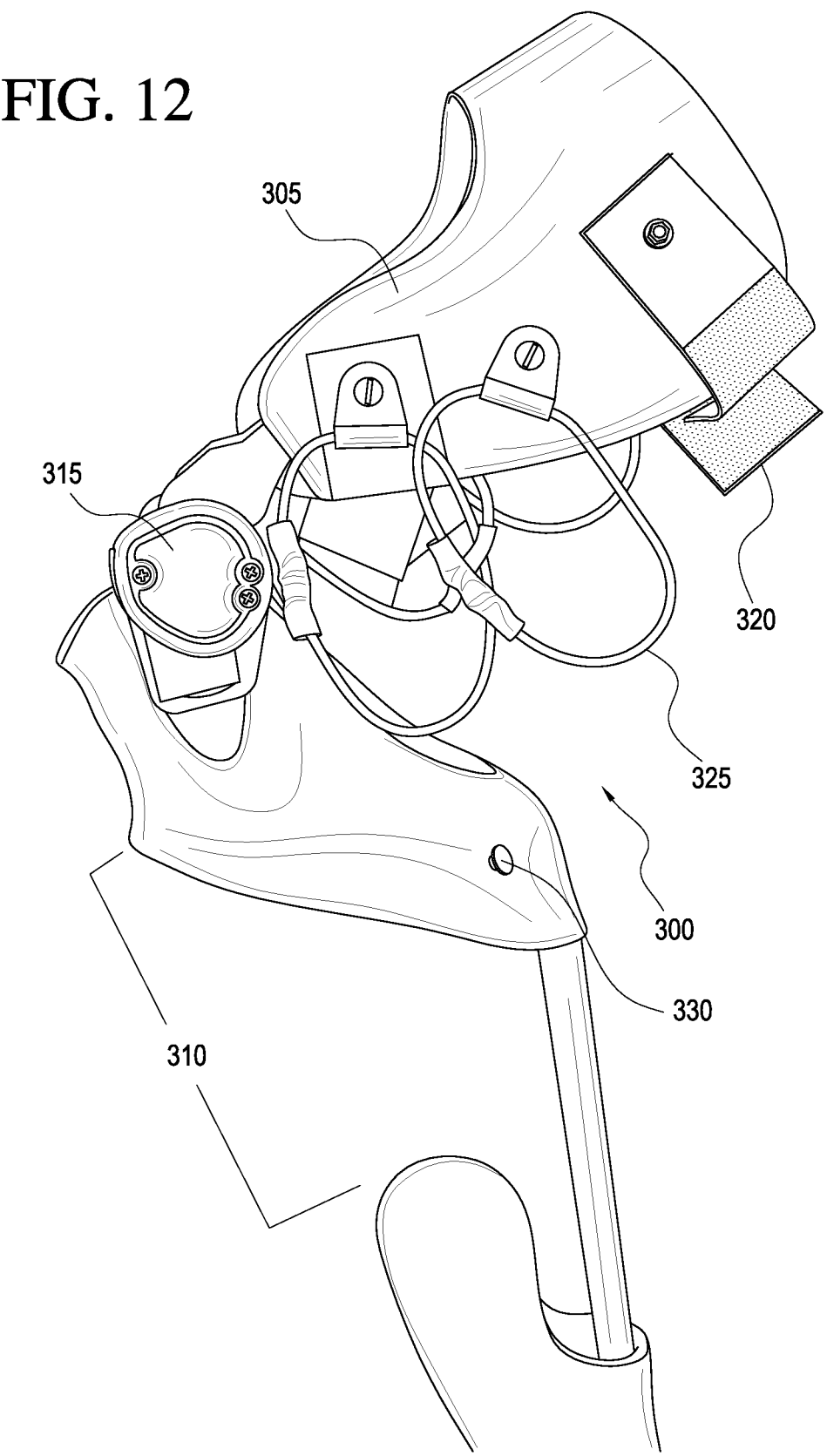
FIG. 12 is a side view of a knee ankle foot exoskeletal orthosis according to another embodiment of the present invention.

With reference now to FIGS. 10-11, an exoskeletal orthosis 100 may comprise a proximal cuff 110, an ankle section/footplate 140, and a single posterior strut 130 (e.g., MEDI CLEVER STRUT) connecting a rear of the proximal cuff to a rear of the ankle section/footplate. In specific embodiments a top of the single posterior strut may be incorporated into a rear of proximal cuff 110 and a bottom of the single posterior strut may be incorporated into a rear of the ankle section/footplate 140. As shown in FIGS. 10-11, the proximal cuff 110 may have at least one strap 120 that at least partially surround two parts of the proximal cuff that are joined by hinge 115 (see also FIG. 2). The at least one strap 120 may have a buckle, clasp, VELCRO®, snap-fit, or other means for adjusting the at least one strap.

In specific embodiments, the single posterior strut 130 may have a tubular or cylindrical shape. The length the single posterior strut may be chosen based on the needs of a patient or user. A longer strut may confer addition flexibility, while a shorter strut may give added support to the user's leg depending on the particular injury. In specific embodiments, the single strut may have a length of between about 5 inches to 13 inches (15.2 cm to 33 cm), for example 7 inches to 11 inches (17.8 cm to 28 cm). Likewise, the diameter of the single posterior strut may be based on at least one of a weight of the user, activity level of the user, or the nature of the user's injury. In specific embodiments, the single posterior strut 130 may comprise at least one of a carbon material, reinforced carbon fiber composition, or resin material.

The single posterior strut embodiment may allow for increased flexibility, for example during walking, and also allows for increased twisting ability, for example during activities requiring rotation (e.g., golf). The single posterior strut embodiment is particularly adaptable to daily use and wear, but not for an extended period of running or strenuous activity. In contrast, a dual strut configuration (e.g., FIG. 3) may be used for strenuous activities.

I. Modified Knee Ankle Foot Orthosis

With reference now to FIGS. 12-15, another embodiment of a knee ankle foot orthosis 300 is shown comprising an upper knee orthosis section 305 or cuff connected to an ankle foot orthosis section 310 (proximal cuff 110, at least one posterior strut 130, and ankle section/footplate 140). In a specific embodiment, the at least one posterior strut may comprise dual posterior struts connecting a rear of the proximal cuff to a rear of the ankle section/footplate.

In specific embodiments, a modified knee ankle foot orthosis 300 may comprise a modular removable version that allows a patient to attach or detach the knee orthosis section 305 to the ankle foot orthosis (AFO) section 310 depending on desired activity and limb stability needs.

A fixed version of the knee ankle orthosis may also be provided in which the upper knee orthosis section 305 and ankle foot orthosis section 310 may be monolithic. The fixed version may be appropriate, for example, for a user who has a spinal cord injury of a permanent knee nerve injury. In one or more embodiments, the fixed version of the knee ankle foot orthosis 300 may comprise a connector or hinge 315 (e.g., Tm5 or original TOWNSEND knee hinges) with an upper knee orthosis section 305 or cuff fused to a lower monolithic exoskeletal ankle foot orthosis section 310.

Figure 13:
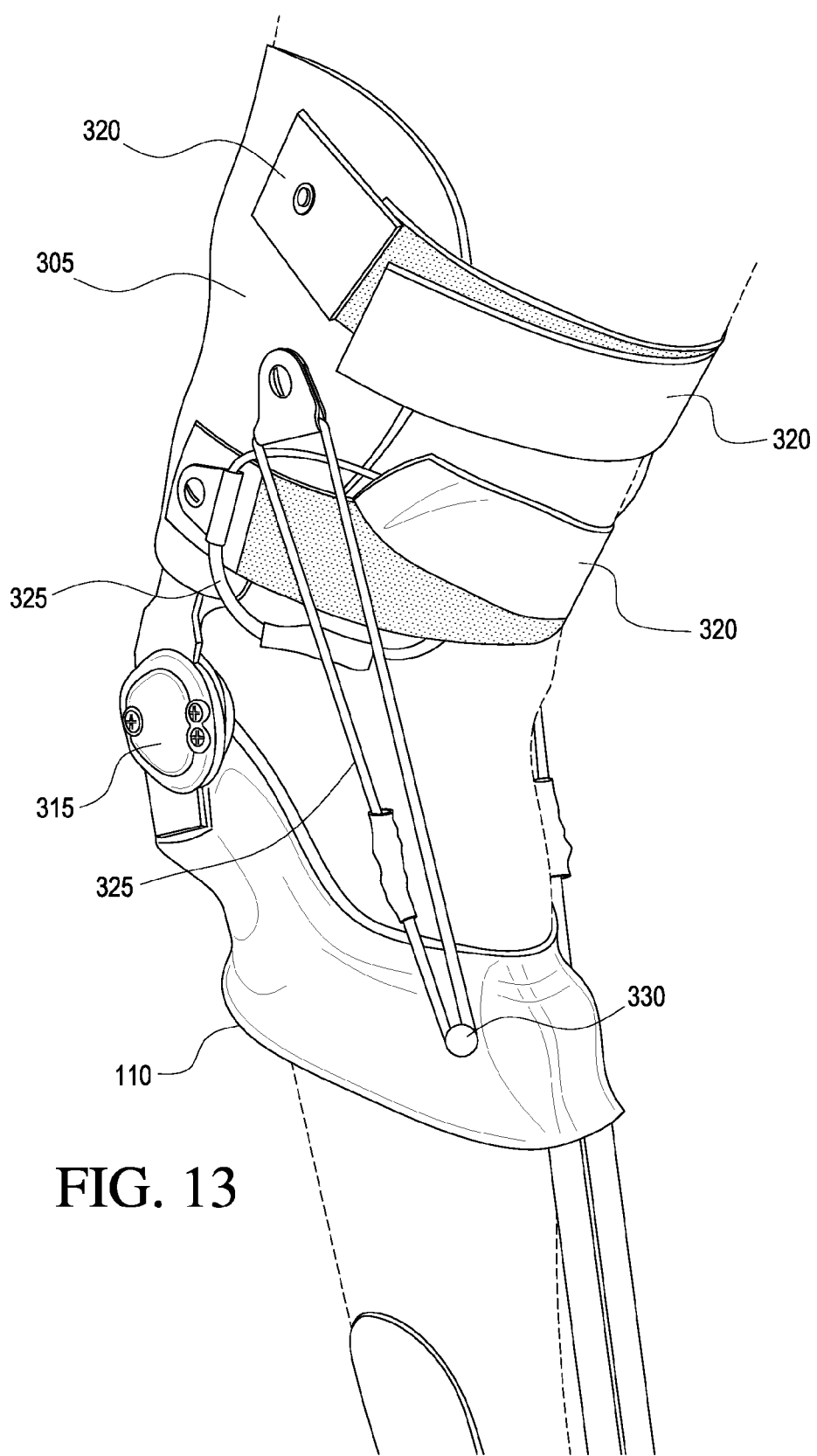
FIG. 13 is a side rear perspective view of the knee ankle foot exoskeletal orthosis according to FIG. 12 in use.

The upper knee orthosis section 305 may comprise at least one strap 320 (for example, two straps as shown in FIG. 13) to at least partially surround both the upper knee ankle orthosis section 305 and a rear a user's leg above the knee, thereby helping affix the upper knee orthosis section 305 to the user. The at least one strap 320 may have a buckle, clasp, VELCRO®, snap-fit, or other means for adjusting the at least one strap.

In FIGS. 12-15, the upper knee orthosis section 305 comprises at least one stretchable band 325 affixed on each side, for example, two stretchable bands 325 affixed on each side. The at least one stretchable band 325 may be fixed at a proximal attachment or a distal attachment on the upper knee orthosis section 305. For example, there may be one stretchable band 325 affixed proximally at or near the posterior of the knee orthosis section between lower and upper straps 320 and another stretchable band 325 affixed distally at or near a side of the knee orthosis section on a lower strap (see e.g., FIG. 13).

In specific embodiments, the at least one stretchable band 325 may comprise a rubber material, an elastic material, or a bungee cord material. In a specific embodiment, the at least one stretchable band may comprise an elastic band adapted from a PHYSIONETICS® VP2 terminal device.

The at least one stretchable band 325 may be attached to the knee ankle orthosis section 305 by an appropriate means including, but not limited to, a bolt, rivet, screw, snap-fit, or pivoting clasp. In a specific embodiment, a pivoting clasp may move or pivot when a user's knee moves.

Figure 14:
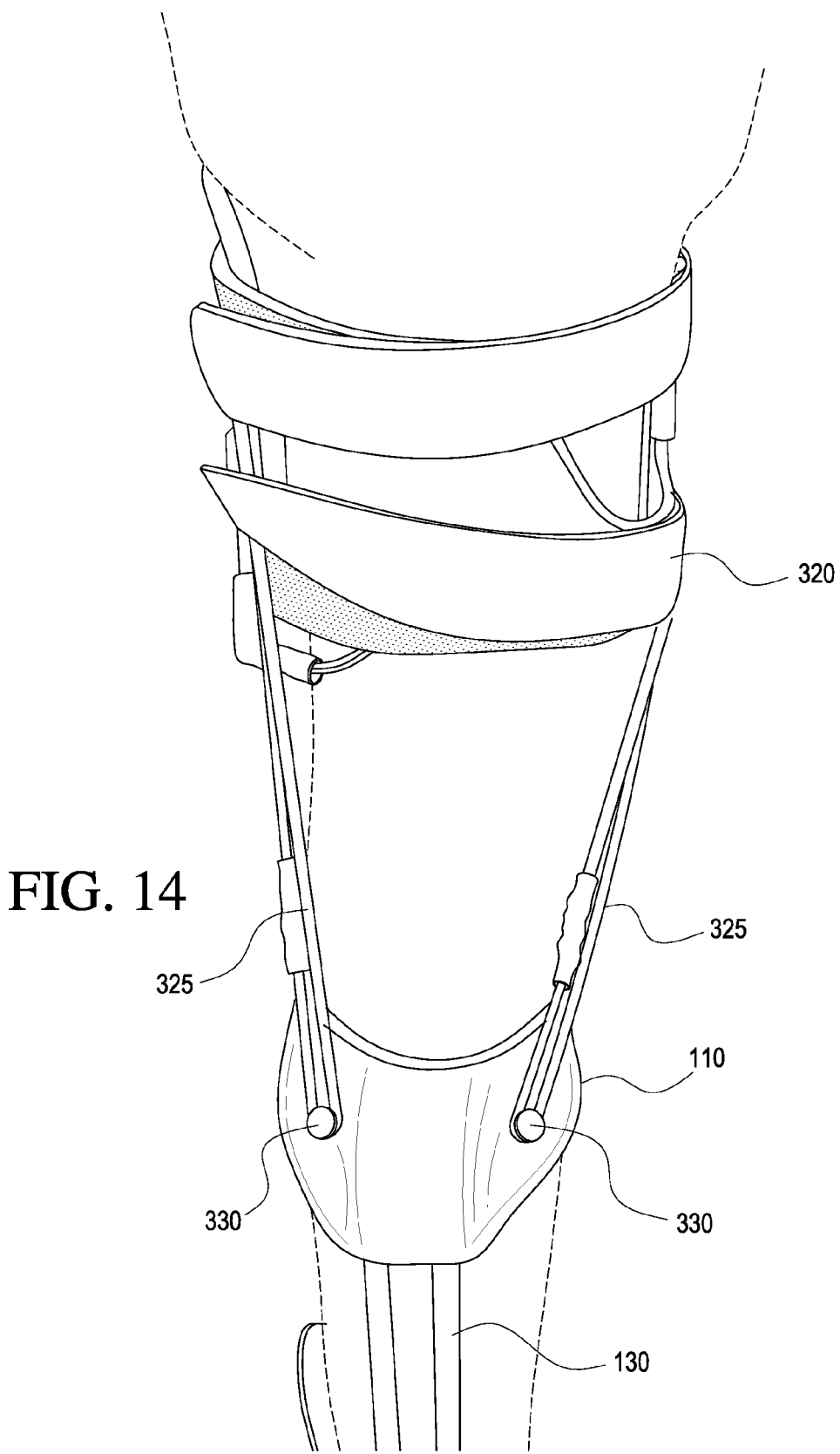
FIG. 14 is a rear view of a knee ankle foot exoskeletal orthosis according to FIG. 13 in use.
Figure 15:
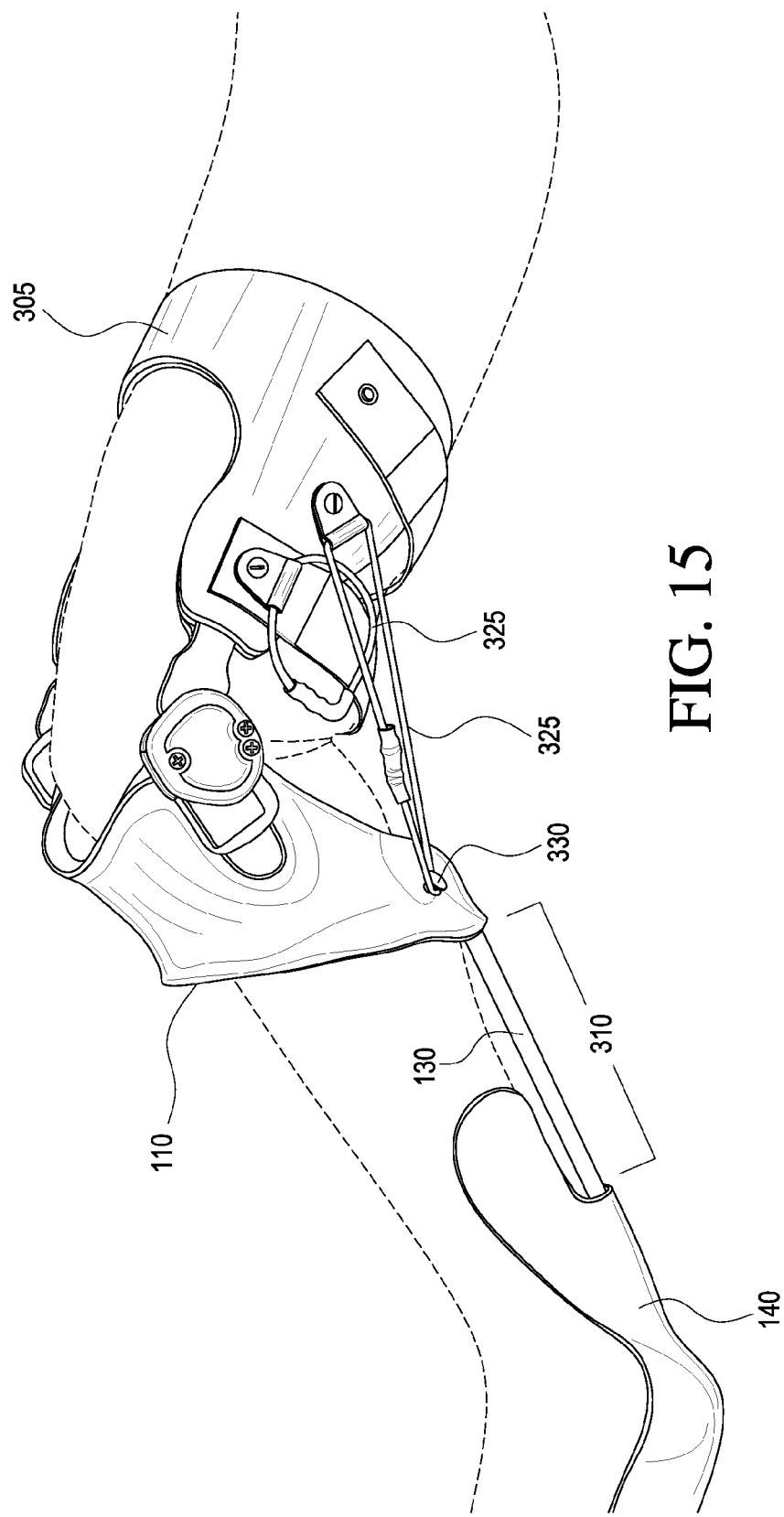
FIG. 15 is a side view of a knee ankle foot exoskeletal orthosis according to FIG. 13 while a user is seated.

When in use, the at least one stretchable band 325 from the upper knee orthosis section 305 may be manually connected to a corresponding fastener or fixing means 330 on the proximal cuff 110 of ankle foot orthosis section 310 (FIGS. 13-15). The corresponding fastener or fixing means 330 may be located at or near a side rear of the proximal cuff. The fastener or fixing means 330 may be any appropriate device and may include, but is not limited to, a bolt, rivet, screw, clasp, and the like. The placement of the fastener or fixing means 330 may help in providing the level of hamstring assist that is required for a patient or user.

A manual connection allows a user or patient to use the at least one stretchable band 325 or to decide not to use the at least one stretchable band 325, depending on the activity, environment, and/or injury. Thus, for example, if there are two stretchable bands on each side of the knee orthosis section 305, a patient may manually connect just one pair of stretchable bands to the ankle foot orthosis section 310 (e.g., FIG. 13).

This embodiment of the knee ankle foot orthosis acts like an artificial hamstring and, in particular, may be helpful to individuals with hamstring injuries or sciatic nerve problems. This version of the knee ankle foot orthosis also allows for backward movement, thereby allowing for a controlled normal type of running.

J. Alignable and Non-Alignable Versions of Orthosis

With reference now to FIGS. 16a-17, in specific embodiments, the exoskeletal orthosis may have an alignable (FIGS. 16a-16b) or a non-alignable (FIG. 17) configuration. Both configurations may be fixed or modular.

The alignable or non-alignable exoskeletal orthosis comprise a proximal cuff; an ankle section/footplate; and at least one posterior strut connecting a rear of the proximal cuff to a rear of the ankle section/footplate. In the alignable configuration, the at least one posterior strut (e.g., dual posterior struts) is connected to at least one of the ankle/footplate or the posterior cuff via a bolt mechanism 400, as shown in FIGS. 16a-16b.

In specific embodiments, the bolt mechanism 400 may comprise at least one threaded bolt 405, a washer 410, and two opposing discs 415, 420. Each of the two opposing discs 415, 420 may have reciprocal curved surfaces (as shown in FIG. 16b) for receiving a posterior strut.

Between a bottom opposing disc 420 and a surface of the ankle/footplate 140, at least one angled wedge 425 may be placed to allow for anteroposterior or lengthwise alignment changes or mediolateral or crosswise alignment changes. The angled wedge 425 may have, for example, about 1-8° rise or incline. A threaded laminate plate 430 for tightening the bolt mechanism may be placed below a surface of the ankle/footplate. In specific embodiments, the laminate plate 430 may have a thickness of 0.2 inches to 0.5 inches (5 mm to 12.7 mm), for example, 0.25 inches to 0.4 inches (6 mm to 10 mm)

FIG. 17 shows a non-alignable configuration in which the at least one posterior strut 130 (e.g., a dual strut configuration) is fixed onto an ankle/footplate 140 and a proximal cuff 110, for example via upper and lower mounting plates 440a, 440b respectively. The upper and lower mounting plates 440a, 440b each have moldable flaps or wings 450, extending from the sides thereof. The moldable flaps or wings 450 may comprise a moldable metal, such as a wire cage or moldable metal band. The moldable flaps or wings 450 allow for contouring and securing the mounting plates and at least one posterior strut to the proximal cuff 110 and/or ankle/footplate 140.

K. Uses

The exoskeletal orthosis is a viable alternative to amputation despite severe impairment of the leg. In addition, the exoskeletal orthosis may allow at least one of: 1) a more normal walking or running pattern for those with severe injury to the leg, ankle, and/or foot that results in decreased ankle range of motion or increased pain; 2) those with an isolated peroneal neuropathy to run; 3) those with tibial neuropathy to walk and run; or 4) increased agility (stepping forward, backward, side-to-side) despite stated physical impairments. The orthosis also promotes use and subsequent strengthening of the quadriceps muscle during everyday activities. The orthosis may also be used for spinal cord injuries in which there is weakness at the ankle and at least 4 out of 5 strength in the knee.

The exoskeletal orthosis of the present invention may be modified to allow safer and more normalized gait pattern during the early postoperative period after leg/foot/ankle surgery instead of the CAM boot (a 'walking boot') The orthosis may also be used as a pediatric device for those with cerebral palsy who have ankle plantarflexion weakness associated with Achilles lengthening procedures and hamstring weakness.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

What is claimed is:

1. An alignable exoskeletal orthosis, comprising:
   a proximal cuff;
   an ankle section/footplate; and
   dual posterior struts connecting a rear of the proximal cuff to a rear of the ankle section/footplate,
   wherein the dual posterior struts are fixed onto at least one of the ankle section/footplate or the proximal cuff via a bolt mechanism comprising two opposing discs, each of the two opposing discs having reciprocal curved surfaces, said reciprocal curved surfaces facing the dual posterior struts configured so that the reciprocal curved surfaces surround at least a portion of a circumference of the dual posterior struts; and
   at least one angled wedge positioned between a bottom opposing disc and a surface of the ankle section/footplate, thereby allowing clamping of the dual posterior struts at different angles and allowing for alignment changes.

2. An orthosis according to claim 1, wherein the dual posterior struts each have a tubular or cylindrical shape.

3. An orthosis according to claim 1, wherein the at least one angled wedge has about a 1 to 8° rise or incline.

4. An orthosis according to claim 1, wherein the dual posterior struts are cylindrical.

5. An alignable exoskeletal orthosis according to claim 1, wherein the ankle section/footplate comprises a threaded laminate plate below an outer surface, and wherein the bolt mechanism further comprises at least one threaded bolt.

* * * * *